United States Patent [19]
Silverman

[11] Patent Number: 5,165,424
[45] Date of Patent: Nov. 24, 1992

[54] METHOD AND SYSTEM FOR WHITENING TEETH

[76] Inventor: Harvey N. Silverman, 3406 Kersdale Rd., Pepper Pike, Ohio 44124

[21] Appl. No.: 564,753

[22] Filed: Aug. 9, 1990

[51] Int. Cl.⁵ .............................................. A61C 7/00
[52] U.S. Cl. .................................. 128/861; 433/215; 433/216
[58] Field of Search .............................. 128/859–862; 433/6, 216, 217.1, 215

[56] References Cited

U.S. PATENT DOCUMENTS

| | | | |
|---|---|---|---|
| 2,833,278 | 5/1958 | Ross | 128/862 |
| 2,835,628 | 5/1958 | Saffir . | |
| 3,060,935 | 10/1962 | Riddell | 433/217.1 X |
| 3,073,300 | 1/1963 | Berghash . | |
| 3,379,193 | 4/1968 | Monaghan | 128/862 |
| 3,657,413 | 3/1972 | Rosenthal . | |
| 3,688,406 | 9/1972 | Porter et al. . | |
| 3,894,286 | 10/1974 | Cowen | 128/861 X |
| 4,064,628 | 12/1977 | Weitzman | 128/861 X |
| 4,150,485 | 4/1979 | Lee, Jr. et al. | 433/217.1 X |
| 4,376,628 | 3/1985 | Aardse | 433/217.1 X |
| 4,944,947 | 7/1990 | Newman | 128/861 X |

FOREIGN PATENT DOCUMENTS 0359135 3/1990 European Pat. Off. ............ 128/859

OTHER PUBLICATIONS

Funk et al, "Fabrication of a Resilient Plastic Interdental Splint" pp. 39-46, vol. IX, No. 1.
Haywood "Nightguard Vital Bleaching", pp. 173 & 175.
Clinical Research Associates, Newsletter—Dec. 1989.
Clinical Research Associates Newsletters—Jul. 1989.

*Primary Examiner*—Robert A. Hafer
*Assistant Examiner*—Kerry Owens
*Attorney, Agent, or Firm*—Shlesinger, Arkwright & Garvey

[57] ABSTRACT

A method for whitening the teeth of a person, comprises the steps of a retainer made of a plastic material adapted to be moldable when heated for conforming to the shape of one of the upper and lower teeth of the person; heating the retainer until soft and moldable without losing its basic shape; fitting the retainer around one of the upper and lower teeth; applying a layer of tooth whitening composition inside the retainer; wearing the loaded retainer for several hours each day until the teeth to be whitened have become whiter; replacing the tooth whitening composition every 1-2 hours; and repeating the above steps with another retainer for the other of lower and upper teeth.

17 Claims, 2 Drawing Sheets

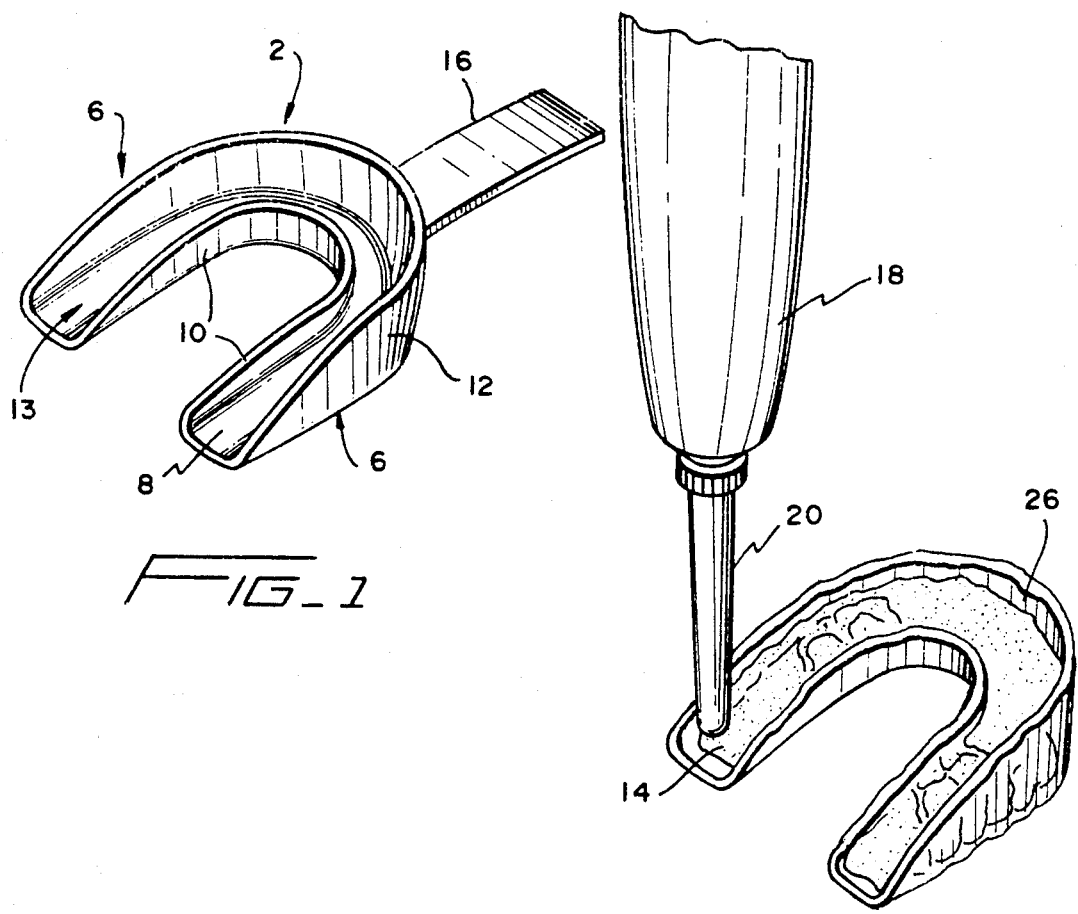
FIG_1
FIG_4
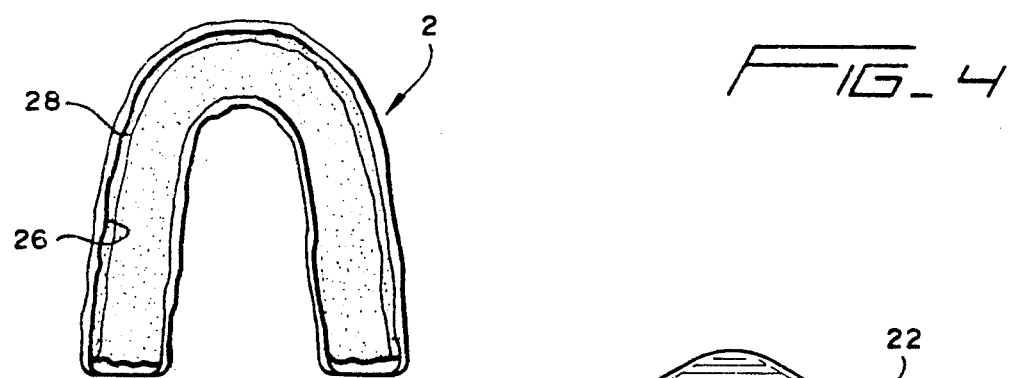
FIG_5
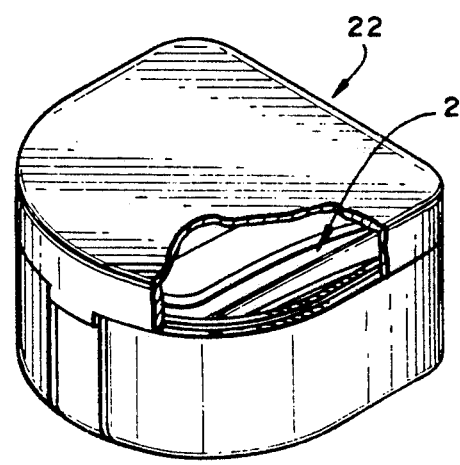
FIG_6

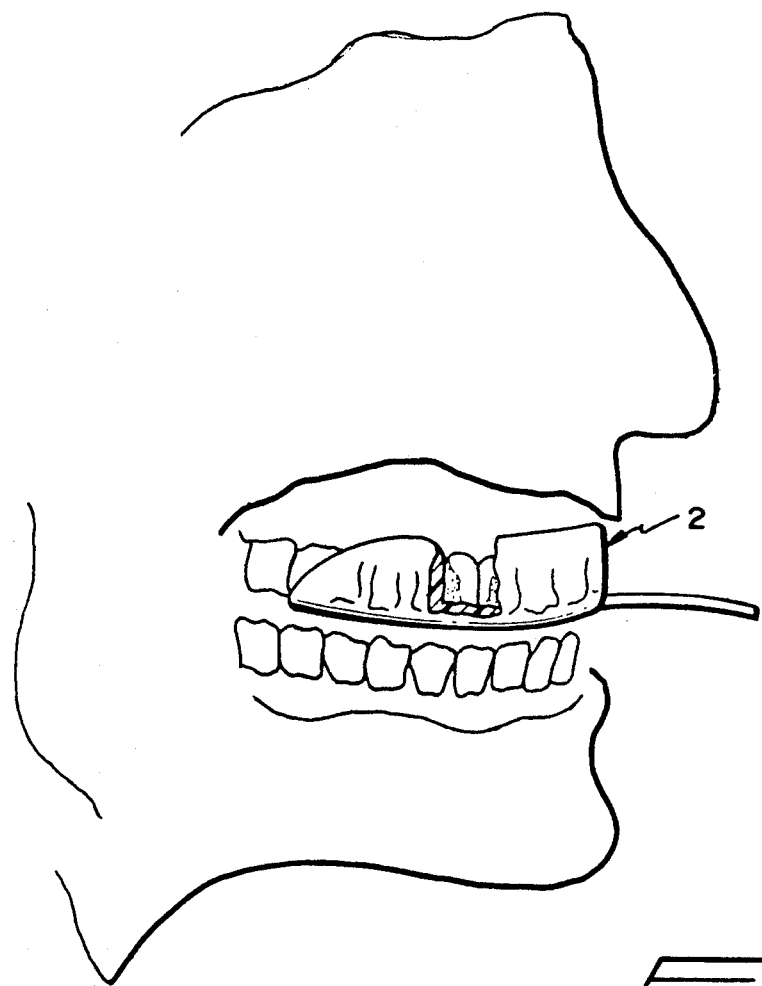
FIG_2
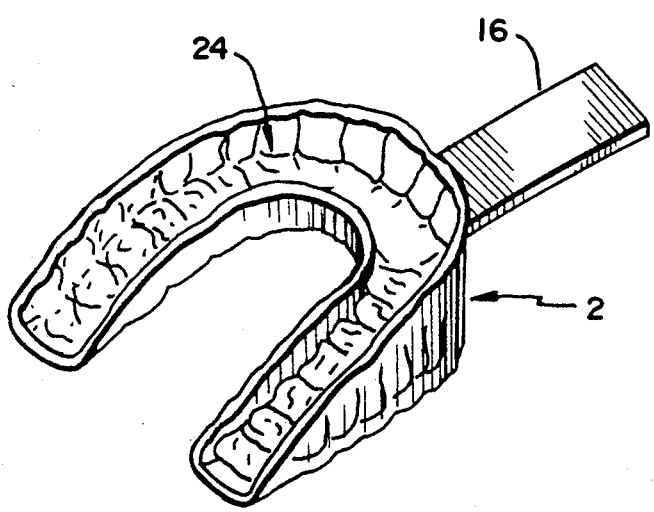
FIG_3

METHOD AND SYSTEM FOR WHITENING TEETH

FIELD OF THE INVENTION

The present invention relates generally to dental treatment and more particularly to a method and system for applying tooth whitening composition to a person's teeth.

BACKGROUND OF THE INVENTION

Many commercially available toothpastes remove stains through abrasives, which can damage the tooth enamel. Toothpastes are unable to whiten teeth that are naturally yellow or gray in color. The present method of obtaining whiter teeth includes tooth bonding, capping or in-office dental bleaching procedures. These methods are relatively costly and therefore not widely available to everyone.

The in-office dental bleaching procedure involves making an alginate impression of the arch to be treated. From the resultant hydrocal cast, a vacuum-formed soft plastic night guard, approximately 2 mm thick, is fabricated. The custom made tray is then used to apply a tooth whitening substance to the teeth to be whitened. The in-office procedure is fairly expensive and therefore not readily available to the consumers.

Tooth whitening substances are currently available in the market. A 10% Carbamide Peroxide, also known as perhydrol-urea, hydrogen peroxide carbamide, urea peroxide, or urea hydrogen peroxide, has been recommended for bleaching teeth. Prior use of the chemical by dental clinics has been as oral antiseptic where tooth bleaching was a side effect of extended contact time. However, application of the substance involves using a cotton tipped applicator or a toothbrush, which does not make it possible for the tooth whitening composition to stay in contact with the tooth for a longer period.

There is therefore a need to provide an apparatus and method for whitening teeth that is fairly inexpensive without requiring a visit to a dentist, that can be used effectively at home and that permits the tooth whitening composition to remain in contact with the teeth to be whitened for a relatively longer period of time.

OBJECTS AND SUMMARY OF THE INVENTION

It is therefore an object of the present invention to provide a method and system for tooth whitening where the tooth whitening substance is permitted to remain in contact with the tooth to be whitened for a relatively longer period of time.

It is another object of the present invention to provide a method and system for tooth whitening where the tooth whitening substance can be applied at home, without requiring a visit to a dentist.

It is still another object of the present invention to provide a method and system for tooth whitening where the tooth whitening substance is carried in a tray which is custom fitted by a user to his teeth at home without a visit to a dentist.

In summary, the present invention provides a method and system for tooth whitening that is relatively inexpensive and permits the tooth whitening substance to remain in contact with the teeth to be whitened for a relatively longer period of time.

These and other objects of the present invention will become apparent from the following detailed description.

BRIEF DESCRIPTIONS OF THE DRAWINGS

FIG. 1 is a top perspective view of a retainer used in the present invention, shown before being custom fitted to a user's teeth.

FIG. 2 is a side elevational view of the retainer of FIG. 1, with portion broken away, shown being custom fitted to a user's upper teeth in accordance with the present invention.

FIG. 3 is a top perspective view of a custom fitted retainer according to the present invention.

FIG. 4 is a top perspective view of the custom fitted retainer of FIG. 3, shown with the attached strap removed and shown with a layer of tooth whitening composition being applied therein in accordance with the present invention.

FIG. 5 is a top plan view of the retainer of FIG. 4 after the application of the tooth whitening composition.

FIG. 6 is a top perspective view of a storage case for the custom fitted retainer of FIG. 3 with the strap removed.

DETAILED DESCRIPTION OF THE INVENTION

A retainer 2 prior to being custom fitted to a user's upper or lower teeth according to the present invention is disclosed in FIG. 1. The retainer 2 is substantially U-shaped in plan view and in cross-section. The retainer 2 is preferably made of tasteless, non-toxic, yieldable, soft, plastic material, such as polyethylene obtainable from Brimns, Inc., Buffalo, N.Y. The retainer 2 becomes soft and moldable when heated so that it can be fitted and molded around the contours of the upper or lower teeth of a user. The retainer 2 has a frontal bite portion 4 and a pair of leg portions 6 extending rearwardly thereof. The retainer 2 includes a bottom wall 8 connected to an inner retaining wall 10 and an outer retaining wall 12 to form a trough 13 for receiving a tooth whitening composition 14, preferably in a gel, as best shown in FIG. 2. A strap 16 is secured to the retainer 2.

The retainer 2 is similar in initial appearance to a mouth guard, such as disclosed in U.S. Pat. No. 3,073,300, which is hereby incorporated by reference. However, the patent does not show the attached strap 16.

A squeeze tube 18 and a nozzle 20 threadedly secured thereto are preferably used to dispense the tooth whitening composition 14. The tooth whitening composition comprises an active ingredient of 10% Carbamide Peroxide (10%), EDTA disodium, citric acid, Carbopol 940, Triethanolamine, glycerin, and flavors. The EDTA disodium and citric acid provide buffering agents and preservatives to maintain taste and effectiveness of the composition 14. The Carbopol 940, Triethanolamine and glycerin form the media in which ingredients are contained. The composition is preferably relatively much thicker, thereby allowing for less occurrence of seepage in the back of the throat. Although the ingredients of the composition 14 are not harmful to the body even if ingested, the consumer must refrain from swallowing the composition 14 during use. A composition similar to the tooth whitening composition 14 is disclosed in U.S. Pat. No. 3,657,413, which is hereby incorporated by reference. Several similar products are presently available in the market.

A plastic case 22 is used to keep the retainer 2 when not in use.

OPERATION OF HOME USE AND APPLICATION

The kit supplied to the consumer includes a pair of retainers 2 for the upper and lower teeth, a tube 18 containing tooth whitening composition 14, a dispensing nozzle 20, and a carrying case 22, preferably one for each of the retainer 2. To use the kit, the retainer 2 is first custom fitted to the person's teeth in a series of steps described below.

A pot of water is brought to a full boil at 212 degrees F. The water is then allowed to sit until it stops boiling. Substantially immediately subsequent to the stopping of the boiling of the water, the retainer 2 is then held by the end of the strap 16 and placed entirely in the hot water and waved back and forth for approximately 5 seconds at substantially sea level. A person of ordinary skill in the art will understand that less immersion time may be required at higher altitudes because of the reduced boiling temperature of water. It is critical that accurate timing be observed. If the retainer 2 is under hot water too long, the material will adhere to itself or lose its basic configuration.

After about at least 5 seconds, the retainer 2 is removed from the hot water and excess water is shaken off. The retainer 2 is then placed immediately around either the upper or lower teeth, centering it around the teeth, as best shown in FIG. 2. The retainer 2 will be warm, but will not burn, since it quickly cools as soon as it is removed from the hot water. The retainer 2 preferably is approximately 0.09 inch thick at the base wall 8 and approximately 0.078 inch thick at the walls 10 and 12 so that it will readily become soft and moldable in a relatively short time and to provide for a comfortable wear.

Without delay, the upper and lower teeth are brought together, biting into the retainer 2; the tongue is pressed against the back of the upper teeth and any air and water from the retainer 2 is sucked out; and the fingers are used to mold the retainer 2 around the upper teeth to make a smooth tight fit, making sure that all of the teeth are covered. A mirror is preferably used for best results. It is important that the upper and lower teeth be brought together and the procedure followed strictly at all times during the forming process in order to properly shape the retainer 2 to the contour of the teeth and gums.

If a good fit is not obtained, the above procedure may be repeated as many times as necessary, provided that the retainer 2 is not kept under hot water longer than five seconds each time.

The retainer 2 is then left in the mouth for approximately 30 seconds and then removed and placed under cold water to retain its new shape. The custom fitted retainer 2 attains teeth impressions 24 after being molded to the shape of the person's teeth, as best shown in FIG. 3. The custom fitter retainer 2 is then tried for comfort. When a good fit is determined, the strap 16 is trimmed with scissors.

All of the upper or lower teeth should be covered by the custom fitted retainer 2. For more comfortable fit or if too much of the gums are covered, the custom fitted retainer 2 may be trimmed with scissors.

The retainer 2 for the other of the lower and upper teeth is fitted in the same way as discussed above.

A very thin layer of the tooth whitening composition 14 is then placed on the inside surfaces of the trough 13 of the custom fitted retainer 2, as best shown in FIG. 4. Preferably, a very thin layer 28 of the tooth whitening composition 14 is applied to the inside surface 26 of the outer wall 6 of the custom fitted retainer 2 such that the composition 14 will be applied to the front surfaces of the teeth to be whitened, as best shown in FIGS. 4 and 5. The tooth whitening composition 14 is used sparingly so that the minimum amount of composition oozes out of the custom fitted retainer 2 when placed around the teeth.

The teeth to be whitened should be brushed before the loaded custom fitted retainer 2 is worn. The custom fitted retainer 2 with the tooth whitening composition 14 is then seated completely and firmly over the teeth. The fingers are used so that the composition 14 covers the surface of the teeth to be whitened. Any excess composition is removed with a facial tissue.

The custom fitted retainer 2 is worn approximately 5 to 18 hours per day. The tooth whitening composition 14 is preferably replaced every 1½ hours. The rate of the whitening process is directly related to the period of use of the custom fitted retainer 2 and the frequency of change of the whitening composition 14. The more the custom fitted retainer 2 is used and the more often the whitening composition is replaced, the faster the whitening process proceeds. If the custom fitted retainer 2 is worn for a good part of the day, the desired color change will occur within one to two weeks. If it is worn for only a few hours daily, the process may take longer. Night time only users sometimes require a little more time to achieve maximum benefits, since the whitening composition 14 is not replaced during sleep.

It is recommended that the user does not wear both custom fitted retainers at the same time. It is also recommended that the consumer use the kit with one of the upper and lower teeth, preferably the upper teeth, until the desired color change is achieved relative to the untreated lower teeth. Treatment for the lower teeth may then proceed after the upper teeth have been whitened to the degree desired by the consumer.

After the custom fitted retainer 2 is taken out of the mouth, the retainer 2 should be rinsed and the teeth should be brushed with a fluoride toothpaste. When not in use, the custom fitted retainer 2 should be kept in its storage case 22.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

I claim:

1. A method for whitening the teeth of a person, comprising the steps of:
   a) providing a retainer made of a plastic material adapted to be moldable when heated for conforming to the shape of one of the upper and lower teeth of the person;
   b) heating the retainer with boiling water until soft and moldable without losing its basic shape;

c) moving the retainer while submerged in boiling water;
d) fitting the retainer around one of the upper and lower teeth;
e) applying a layer of tooth whitening composition inside the retainer;
f) wearing the loaded retainer for several hours each day until the teeth to be whitened have become whiter;
g) replacing the tooth whitening composition periodically;
h) repeating the above steps with another retainer for the other of the lower and upper teeth.

2. A method as in claim 1, wherein:
a) said heating step comprises heating the retainer with boiling water for approximately 5 seconds.

3. A method as in claim 1, wherein said fitting step comprises the steps of:
a) biting firmly into the retainer immediately after said heating step;
b) pressing the tongue against the back of the upper teeth;
c) sucking out any air from the first retainer; and
d) using the fingers to mold the retainer around the front of one of the upper and lower teeth.

4. A method for whitening teeth as in claim 3 and further comprising the step of:
a) keeping the retainer in the mouth for substantially at least 30 seconds after said step of using the fingers to mold the retainer.

5. A method for whitening teeth as in claim 4 and further comprising the step of:
a) removing the retainer from the mouth after said step of keeping the retainer in the mouth; and
b) dipping the retainer in cold water.

6. A method as in claim 1, wherein:
a) said fitting step comprises trimming the retainer of any excess material.

7. A method as in claim 1, wherein:
a) said applying step comprises applying a layer of the tooth whitening composition along an inside front surface of the retainer.

8. A method for whitening teeth as in claim 1 wherein:
a) said step of wearing comprises wearing the loaded retainer approximately 5-18 hours per day; and
b) said step of replacing comprises replacing the tooth whitening composition approximately every 1-2 hours.

9. A method as in claim 1, and further comprising the step of:
a) brushing the teeth before placing the loaded retainer in the mouth.

10. A method as in claim 8, and further comprising the step of:
a) brushing the teeth with fluoride toothpaste after taking the loaded retainer from the mouth.

11. A system for whitening teeth of a person, comprising:
a) a custom fitting U-shaped retainer made of a material adapted to be moldable when heated for conforming to the shape of the upper or lower teeth of the person, said retainer being custom fitted by heating said retainer prior to fitting around the upper or lower teeth;
b) said retainer including a front bite portion and a pair of rearwardly extending leg portions therefrom;
c) said member including inner and outer retaining walls and a connecting base portion for forming a trough;
d) tooth whitening composition disposed in said trough;
e) said composition consisting of 10% Carbamide Peroxide, EDTA disodium, citric acid, Carbopol 940, Triethanolamine, glycerin, and flavors;
f) whereby when said retainer loaded with said tooth whitening composition is worn by the person, said composition comes in contact with the teeth to be whitened.

12. A system as in claim 11, wherein:
a) said trough includes front inside surface; and
b) said composition is disposed on said inside surface.

13. A system as in claim 13, wherein:
a) said composition comprises 10% Carbamide Peroxide.

14. A system as in claim 11, wherein:
a) said retainer has a thickness range of approximately 0.078-0.09 inch.

15. A kit for whitening the teeth of a person, comprising:
a) a U-shaped retainer for each of the upper and lower teeth of a person, said retainer being made of a material such that said retainer is moldable when heated prior to fitting to the shape of the upper or lower teeth;
b) said retainer including a front bite portion and rearwardly extending leg portions;
c) said retainer including inner and outer retaining walls and a connecting base portion for forming a trough for receiving a tooth whitening composition;
d) a dispenser for said tooth whitening composition;
e) tooth whitening composition comprising 10% Carbamide Peroxide; and
f) a case for said retainer.

16. A kit as in claim 15, wherein:
a) said composition consists of 10% Carbamide Peroxide, EDTA disodium, citric acid, Carbopol 940, Triethanolamine, glycerin, and flavors.

17. A kit as in claim 15, wherein:
a) said retainer has a thickness range of approximately 0.078-0.09 inch.

* * * * *